US009446074B2

(12) United States Patent
Kishikawa et al.

(10) Patent No.: US 9,446,074 B2
(45) Date of Patent: Sep. 20, 2016

(54) METHOD OF PREPARING PLATELET SOLUTION REPLACED WITH ARTIFICIAL PRESERVATION SOLUTION

(71) Applicant: Toray Industries, Inc., Tokyo (JP)

(72) Inventors: Tatsuya Kishikawa, Otsu (JP); Masahiro Osabe, Otsu (JP); Yoshiyuki Ueno, Otsu (JP); Masaaki Shimagaki, Urayasu (JP); Shigenori Tanaka, Ibaraki (JP); Tomoya Hayashi, Ibaraki (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 14/647,856

(22) PCT Filed: Nov. 27, 2013

(86) PCT No.: PCT/JP2013/081922
§ 371 (c)(1),
(2) Date: May 28, 2015

(87) PCT Pub. No.: WO2014/084263
PCT Pub. Date: Jun. 5, 2014

(65) Prior Publication Data
US 2015/0313943 A1 Nov. 5, 2015

(30) Foreign Application Priority Data
Nov. 30, 2012 (JP) .................................. 2012-261982

(51) Int. Cl.
*A61K 35/14* (2015.01)
*C12N 5/00* (2006.01)
(Continued)

(52) U.S. Cl.
CPC ................. *A61K 35/19* (2013.01); *A61M 1/34* (2013.01); *B01D 61/147* (2013.01); *B01D 63/02* (2013.01); *B01D 71/44* (2013.01); *B01D 71/68* (2013.01); *B01D 2315/10* (2013.01); *B01D 2325/36* (2013.01)

(58) Field of Classification Search
None
See application file for complete search history.

(56) References Cited

U.S. PATENT DOCUMENTS 5,102,407 A * 4/1992 Carmen .............. A61M 1/0209
210/411
5,753,428 A * 5/1998 Yuasa .................. A01N 1/0226
424/93.72

(Continued)

FOREIGN PATENT DOCUMENTS

JP 54-015476 A 2/1979
JP 61-238834 A 10/1986
(Continued)

*Primary Examiner* — Chris R Tate
*Assistant Examiner* — Douglas F White
(74) *Attorney, Agent, or Firm* — DLA Piper LLP (US)

(57) ABSTRACT

A method of producing a platelet solution replaced with an artificial preservation solution includes a filtering step of carrying out cross-flow filtration of a platelet solution under the conditions of Formula (1) at an inlet wall shear rate of 25 to 1500 $s^{-1}$ using a separation membrane whose surface which contacts with the platelet solution has an average pore size of not less than 0.1 μm and less than 2.0 μm, thereby obtaining a concentrated platelet solution; and a mixing step of mixing the concentrated platelet solution with an artificial preservation solution to obtain the platelet solution replaced with an artificial preservation solution:

$$1.0\times10^{11} < (A\times B)/(\gamma\times\mu_P) \leq 2.5\times10^{13} \text{ (platelets/(hr·m}^2\text{·Pa))} \quad (1)$$

A: Concentration of platelets contained in the platelet solution (platelets/mL; with the proviso that the range is $8.0\times10^7$ to $200\times10^7$ platelets/mL)
B: Filtration flow rate per unit area (mL/hr/m$^2$)
γ: Inlet wall shear rate ($s^{-1}$)
$\mu_P$: Viscosity of the platelet solution (Pa·s).

9 Claims, 1 Drawing Sheet

(51) Int. Cl.
*C12N 5/02* (2006.01)
*A61K 35/19* (2015.01)
*B01D 71/68* (2006.01)
*B01D 71/44* (2006.01)
*A61M 1/34* (2006.01)
*B01D 63/02* (2006.01)
*B01D 61/14* (2006.01)

(56) References Cited

U.S. PATENT DOCUMENTS 7,140,497 B2 * 11/2006 Verpoort ............. A61M 1/0209
 210/500.1

2011/0076669 A1 * 3/2011 Sehgal ................. A01N 1/0226
 435/2

FOREIGN PATENT DOCUMENTS

| | | |
|---|---|---|
| JP | 62-290469 | 12/1987 |
| JP | 62-290469 A | 12/1987 |
| JP | 08-165245 A | 6/1996 |
| JP | 2006-077136 A | 3/2006 |
| JP | 2007-319542 A | 12/2007 |
| JP | 2012-143554 A | 8/2012 |
| JP | 2012-176081 A | 9/2012 |
| WO | 2013/147001 A1 | 10/2013 |

* cited by examiner

Fig. 1A
Fig. 1B
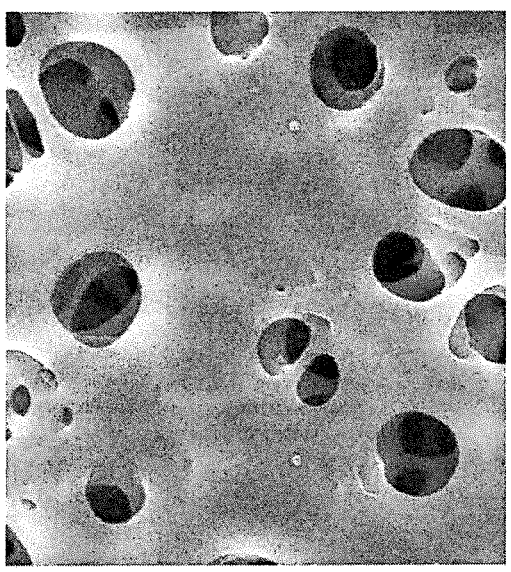 

METHOD OF PREPARING PLATELET SOLUTION REPLACED WITH ARTIFICIAL PRESERVATION SOLUTION

TECHNICAL FIELD

This disclosure relates to a method of producing a platelet solution replaced with an artificial preservation solution.

BACKGROUND

Blood donation for transfusion or production of blood products can be roughly divided into whole blood donation and blood component donation. By separating blood collected by blood donation into each component, various types of blood products are produced. A platelet preparation is a solution in which concentrated platelets are dispersed in blood plasma (containing proteins and water as major components). Since the concentration of platelets in a platelet preparation is 3 times or more higher than that in whole blood, the platelets may very easily aggregate with each other.

Platelet preparations are used for transfusions to prevent or treat bleeding in thrombocytopenia or impaired platelet function. Current platelet preparations may cause allergic reactions such as urticaria or fever in some patients. Proteins contained in the platelet preparations are suggested to be main causes for the allergy, and a platelet solution replaced with an artificial preservation solution, prepared by removing blood plasma containing the proteins and replacing the blood plasma with an artificial preservation solution, has therefore been demanded.

A method of producing a platelet solution replaced with an artificial preservation solution should be a method which does not cause activation of platelets during an operation, and can achieve a high platelet recovering rate and high protein-removing rate. Conventionally, centrifugation has been commonly employed as a method of removing proteins from a platelet preparation. It has been suggested that, when proteins in a platelet preparation are removed by centrifugation, activation of platelets may occur. Moreover, it is said that centrifugation requires a laborious operation and a substantial length of time. However, methods other than centrifugation are not practically used at present.

Examples of other methods include methods based on separation using a membrane. Examples of the membrane separation methods include known techniques used in, for example, separation of blood cells (erythrocytes, leukocytes, and platelets) from blood plasma (JP S62-290469 A, JP S54-15476 A and JP S61-238834 A). JP '469 focuses attention on the swelling property of a membrane for prevention of hemolysis of erythrocytes, and discloses a technique in which a material which hardly swells is used for a porous membrane, and a minimum content of water is used to wet the porous membrane. JP '476 discloses a technique that defines the fibrillar structure of the membrane and increases the blood flow rate. JP '834 focuses attention on a hydrophilic polymer, and discloses, as a membrane which is less likely to cause clogging or fouling, a polysulfone resin porous membrane containing the hydrophilic polymer at 3 to 30% by mass. In those techniques, the subject to be filtered is whole blood, and is not a solution prone to aggregation such as a platelet preparation. Those techniques focus attention only on membranes, and neither discovery nor suggestion on a separation method can be found in them.

It could therefore be helpful to provide novel means of producing a platelet solution replaced with an artificial preservation solution, which means achieves a platelet-activation-suppressing capacity, high platelet recovering performance, and high blood-plasma-removing performance.

SUMMARY

We discovered that production of a platelet solution replaced with an artificial preservation solution is very difficult by using conventional separation membranes for dialysis treatment or apheresis therapy. A possible cause for the difficulty is inappropriate design of the membrane structure. Membranes conventionally used for blood purification are prepared for the purpose of removing low-molecular-weight substances such as urea and some proteins from whole blood containing as major components erythrocytes, leukocytes, platelets, and proteins. Thus, proteins having high molecular weights cannot be removed.

When such a membrane was used to remove more proteins at a filtration rate higher than the rate used under the original working conditions, filtration stopped in the middle of the process. This was due to clogging of the membrane in its inside with proteins, which then caused formation of a deposition layer (cake) containing platelets and proteins on the surface of the membrane, resulting in interruption of filtration.

Occurrence of the clogging and formation of the cake were caused due to the fact that the pores on the surface of the membrane were small, and proteins having high molecular weights therefore remained on the surface of the membrane or inside the membrane without passing through the membrane, and that inappropriate design of the filtration flow rate led to deposition of a large amount of platelets on the surface of the membrane. Interruption of filtration resulted in a decrease in the amount of proteins removed, increase in the platelet loss, and increase in activated platelets.

Thus, we discovered that separation conditions need to be set using a separation membrane having a structure suitable for the platelet solution and object of the separation. However, the membrane design and separation conditions to remove proteins contained in a platelet solution have not been studied. In view of this, further discovered separation conditions under which a high platelet recovering performance and high blood-plasma-removing performance can be achieved without activating platelets.

We thus provide a method of producing a platelet solution replaced with an artificial preservation solution, the method comprising:

a filtering step of carrying out cross-flow filtration of a platelet solution under the conditions of Formula (1) at an inlet wall shear rate of 25 to 1500 s$^{-1}$ using a separation membrane whose surface which contacts with the platelet solution has an average pore size of not less than 0.1 µm and less than 2.0 µm, thereby obtaining a concentrated platelet solution; and a mixing step of mixing the concentrated platelet solution with an artificial preservation solution to obtain the platelet solution replaced with an artificial preservation solution:

$$1.0 \times 10^{11} < (A \times B)/(\gamma \times \mu_P) \leq 2.5 \times 10^{13} \text{ (platelets/} (\text{hr} \cdot \text{m}^2 \cdot \text{Pa})) \quad (1)$$

A: Concentration of platelets contained in the platelet solution (platelets/mL; with the proviso that the range is $8.0 \times 10^7$ to $200 \times 10^7$ platelets/mL)

B: Filtration flow rate per unit area (mL/hr/m$^2$)

γ: Inlet wall shear rate (s$^{-1}$)

$\mu_P$: Viscosity of the platelet solution (Pa·s).

We also provide a method of producing a platelet solution replaced with an artificial preservation solution, the method comprising:

a filtering step of carrying out cross-flow filtration of a platelet solution under the conditions of Formula (1) at an inlet wall shear rate of 25 to 1500 s$^{-1}$ using a separation membrane whose surface which contacts with the platelet solution has an average pore size of not less than 0.1 μm and less than 2.0 μm, thereby obtaining a concentrated platelet solution;

a recovering step of bringing an artificial preservation solution into contact with the separation membrane to recover, into the artificial preservation solution, platelets which have not been recovered into the concentrated platelet solution in the filtering step, thereby obtaining a platelet-containing artificial preservation solution; and a mixing step of mixing the platelet artificial preservation solution with the concentrated platelet solution, thereby obtaining the platelet solution replaced with an artificial preservation solution:

$$1.0\times10^{11} < (A\times B)/(\gamma\times\mu_P) \leq 2.5\times10^{13} \text{ (platelets/(hr·m}^2\text{·Pa))} \quad (1)$$

A: Concentration of platelets contained in the platelet solution (platelets/mL; with the proviso that the range is $8.0\times10^7$ to $200\times10^7$ platelets/mL)
B: Filtration flow rate per unit area (mL/hr/m$^2$)
γ: Inlet wall shear rate (s$^{-1}$)
μP: Viscosity of the platelet solution (Pa·s).

Preferably, in the platelet solution replaced with an artificial preservation solution obtained by the production method described above, the protein removal rate (calculated taking the protein concentration in the original platelet solution as 100) is not less than 60%, and, in addition, the ratio of CD62P-positive platelets of the platelet solution replaced with an artificial preservation solution is not more than 60%. More preferably, the protein removal rate is not less than 65%, and the ratio of CD62P-positive platelets in the platelet solution replaced with an artificial preservation solution is not more than 40%. A higher ratio of CD62P-positive platelets means that the platelets are more activated.

The transmembrane pressure difference in the filtration step is preferably not more than $5.0\times10^3$ Pa, and the permeation performance of the separation membrane is preferably 35 to 150 mL/hr/m$^2$/Pa.

The separation membrane is preferably a hollow fiber membrane. The cross-flow filtration is preferably an internal-pressure-type cross-flow filtration. The inner diameter of the hollow fiber membrane is preferably 100 to 500 μm. The effective length of the hollow fiber membrane is preferably 5 to 50 cm. The separation membrane preferably contains a hydrophilic polymer(s), and the abundance of the hydrophilic polymer(s) on the surface of the separation membrane which contacts with the platelet solution, as measured by X-ray photoelectron spectroscopy at a measurement angle of 90°, is preferably 30 to 60% by mass.

We also provide a method of producing a concentrated platelet solution, the method comprising:

a filtering step of carrying out cross-flow filtration of a platelet solution under the conditions of Formula (1) at an inlet wall shear rate of 25 to 1500 s$^{-1}$ using a separation membrane whose surface which contacts with the platelet solution has an average pore size of not less than 0.1 μm and less than 2.0 μm, thereby obtaining the concentrated platelet solution:

$$1.0\times10^{11} < (A\times B)/(\gamma\times\mu_P) \leq 2.5\times10^{13} \text{ (platelets/(hr·m}^2\text{·Pa))} \quad (1)$$

A: Concentration of platelets contained in the platelet solution (platelets/mL; with the proviso that the range is $8.0\times10^7$ to $200\times10^7$ platelets/mL)
B: Filtration flow rate per unit area (mL/hr/m$^2$)
γ: Inlet wall shear rate (s$^{-1}$)
μ$_P$: Viscosity of the platelet solution (Pa·s).

According to the method of producing a platelet solution replaced with an artificial preservation solution, a high platelet recovery rate and high protein removal rate can be achieved while suppressing activation of platelets even when a platelet solution prone to aggregation such as a platelet preparation, not whole blood, is used. Thus, a high-quality platelet solution replaced with an artificial preservation solution can be produced.

BRIEF DESCRIPTION OF THE DRAWINGS

FIG. 1A is an example of scanning electron micrographs of the inner surface (surface which contacts with blood) of the hollow fiber membranes used in Examples, taken at a magnification of 10,000×.

FIG. 1B is an example of scanning electron micrographs of the inner surface (surface which contacts with blood) of the hollow fiber membranes used in the Examples, which were taken at a magnification of 10,000× and binarized by painting.

DETAILED DESCRIPTION

The term "platelet solution" is a liquid in which platelets and proteins are dispersed in a medium containing blood plasma, which liquid is substantially free of erythrocytes and leukocytes. The medium is typically blood plasma, and may partially contain a buffer such as an artificial preservation solution. The platelet concentration in the platelet solution is $8.0\times10^7$ to $200\times10^7$ platelets/mL. The platelet solution can be obtained by removing erythrocytes and leukocytes from whole blood by a method such as centrifugation followed by filtration through a leukocyte removal filter. Preparations generally known as platelet preparations are preparations in which concentrated platelets are dispersed in blood plasma, and such a preparation may be subjected as it is to the method as the "platelet solution" as long as the platelet concentration is within the range described above. In addition, a liquid prepared by replacing a part of the blood plasma contained in a platelet preparation with an artificial preservation solution, or a liquid prepared by diluting a platelet preparation by mixing it with an artificial preservation solution beforehand may also be used as the platelet solution. As is well known, blood plasma means a component which remains after removal of erythrocytes, leukocytes and platelets from whole blood by a method such as centrifugation, and proteins and water are contained therein as the major components.

The "artificial preservation solution" is an artificial (non-naturally occurring) solution that can be used as a medium to disperse platelets. Artificial preservation solution for platelets are known, and specific examples of the artificial preservation solution include solutions commonly used as infusion solutions such as PAS III-M, M-sol, physiological saline and BICANATE (registered trademark); and solutions containing citric acid such as ACD-A solution. However, the "artificial preservation solution" is not limited to these, and any solution having a performance suitable to preserve platelets, that is, any solution that does not induce generation of an aggregate or destruction of platelets due to osmotic pressure or the like upon contact with platelets, may be used as the "artificial preservation solution."

The "platelet solution replaced with an artificial preservation solution" means a solution prepared by replacing a large part of the medium of a platelet solution with an artificial preservation solution. By the replacement of the medium, which is mainly composed of blood plasma, with the artificial preservation solution, the amount of proteins in the platelet solution is largely reduced. By the above-described method of producing a platelet solution replaced with an artificial preservation solution, a platelet solution replaced with an artificial preservation solution can be obtained by a process which prevents activation of platelets and allows desirable removal of proteins. In the above-described method of producing a platelet solution replaced with an artificial preservation solution, the protein removal rate is preferably not less than 60% and, in addition, the ratio of CD62P-positive platelets in the platelet solution replaced with an artificial preservation solution is preferably not more than 60%. The protein removal rate is more preferably not less than 65%, and the ratio of CD62P-positive platelets in the platelet solution replaced with an artificial preservation solution is more preferably not more than 40%. A higher ratio of CD62P-positive platelets means that the platelets are more activated. When the ratio of CD62P-positive platelets is not less than 60%, aggregation of platelets easily occurs to cause a decrease in the platelet function. A production method that does not cause activation is thus important. When the ratio of CD62P-positive platelets is too low, the aggregation function of platelets may be deteriorated. Thus, the ratio of CD62P-positive platelets in the platelet solution replaced with an artificial preservation solution is preferably not less than 1%, more preferably not less than 3%. The ratio of the increase in the ratio of CD62P-positive platelets in the platelet solution replaced with an artificial preservation solution, calculated taking the ratio of CD62P-positive platelets in the original platelet solution as 1, is not more than 3.0, preferably not more than 2.0, more preferably not more than 1.5.

In the method of producing a platelet solution replaced with an artificial preservation solution, cross-flow filtration of a platelet solution is carried out under the conditions of Formula (1) at an inlet wall shear rate of 25 to 1500 s$^{-1}$ using a separation membrane whose surface which contacts with the platelet solution has an average pore size of not less than 0.1 μm and less than 2.0 μm. By concentrating the platelet solution under such conditions, removal of proteins can be achieved at high efficiency while suppressing activation of platelets.

$$1.0 \times 10^{11} < (A \times B)/(\gamma \times \mu_P) \leq 2.5 \times 10^{13} \text{ (platelets/(hr·m}^2\text{·Pa))} \quad (1)$$

A: Concentration of platelets contained in the platelet solution [platelets/mL] (with the proviso that the range is $8.0 \times 10^7$ to $200 \times 10^7$ platelets/mL)
B: Filtration flow rate per unit area [mL/hr/m$^2$]
γ: Inlet wall shear rate [s$^{-1}$]
$\mu_P$: Viscosity of the platelet solution [Pa·s]

The biggest problem in preparation of a platelet solution from which blood plasma has been removed by filtration is clogging of a membrane with proteins and platelets. When the average pore size on the surface of the membrane is not less than 0.1 μm and less than 2.0 μm, the cause of the clogging is deposition of platelets on the surface which results in formation of a deposition layer containing platelets and proteins. This deposition layer is called "cake." Formation of a cake causes a decrease in the efficiency of removal of blood plasma. Moreover, since the platelets present in the cake cannot be completely recovered, the recovery rate of platelets also decreases. Furthermore, the platelets in the cake release activation factors to cause activation of the recovered platelets, which is also problematic. Thus, it is important to suppress formation of a cake during the filtration of the platelet solution. The recovery rate of platelets is preferably not less than 80%, more preferably not less than 85%, still more preferably not less than 90%.

We discovered that the most suitable filtration method of suppressing formation of a cake is cross-flow filtration. Cross-flow filtration means a filtration method in which only a part of the platelet solution is filtered while the remaining part is allowed to flow as it is (allowed to flow on the surface of the separation membrane without passing through the separation membrane), thereby allowing two flows, that is, a flow vertical to the membrane surface and a flow parallel to the membrane surface, to be present. For example, in a cross-flow filtration using a hollow fiber membrane, the platelet solution is fed from one side of the hollow fiber membrane, and a part of the platelet solution is then filtered while the platelet solution left unfiltered is discharged from the other side.

The filtration flow vertical to the membrane promotes formation of a cake, while the flow parallel to the membrane surface suppresses formation of a cake. Focusing attention on these two flows, we discovered that formation of the cake can be suppressed by carrying out filtration with settings that satisfy the conditions of Formula (1), while controlling the flow rate.

In Formula (1), the numerator (A×B) corresponds to the force which causes formation of a cake, and the denominator ($\gamma \times \mu_P$) corresponds to the force which suppresses formation of a cake. The smaller (A×B) relative to ($\gamma \times \mu_P$), the less likely a cake is to be generated, leading to prevention of activation of platelets and more stable removal of proteins at a higher platelet recovery rate. As can be seen from Formula (1), when the ratio between the cake-forming force and the suppressive force ((A×B)/($\gamma \times \mu_P$)) is more than $1.0 \times 10^{11}$ and not more than $2.5 \times 10^{13}$, the filtration can be carried out while suppressing formation of a cake on the separation membrane. When (A×B) is too small relative to ($\gamma \times \mu_P$), filtration of proteins is insufficient. Thus, the ratio between the cake-forming force and the suppressive force is more preferably more than $1.0 \times 10^{11}$ and not more than $2.0 \times 10^{13}$, still more preferably more than $1.0 \times 10^{11}$ and not more than $1.5 \times 10^{13}$.

When a hollow fiber membrane is used as the separation membrane, the inlet wall shear rate γ can be calculated as follows:

$$\gamma(s^{-1}) = 4 \times C/D \quad (2)$$

C: Linear velocity of the liquid supplied (m/s)
D: Equivalent radius (m).
C in Formula (2) is given by Formula (3):

$$C = (E/1,000,000)/(F \times \text{number of hollow fibers}) \quad (3)$$

E: Flow rate of the platelet solution supplied (mL/s)
F: Cross-sectional area of the platelet solution contacting with the membrane, in the direction vertical to the direction of the flow of the unfiltered platelet solution (m$^2$).

The "platelet solution contacting with the membrane" means the platelet solution continuously present in the vertical direction on the membrane surface in contact with the platelet solution. In a hollow fiber membrane, F is the area of the lumen portion in the cross-section of the hollow fiber membrane.

D in Formula (2) is given by Formula (4):

$$D = 2 \times (F/G) \quad (4)$$

G: Total length of the portion in contact with the wall surface on the outer periphery of the cross-section described above for F (m).

In a hollow fiber membrane, G is the circumferential length of the lumen portion in the cross-section.

As for the flow rate of the platelet solution supplied to the membrane, the solution may be fed at a constant rate or fed at a constant pressure. When the platelet solution is fed using a pump or the like at a constant rate, the amount of physiological saline that flows in 1 minute may be regarded as the flow rate of the platelet solution, E, in Formula (3). When the platelet solution is fed at a constant pressure, the flow rate of the platelet solution, E, can be calculated according to Formula (5):

$$E = H \times (\mu_P / \mu_w) \quad (5)$$

H: Amount of physiological saline that flows in 1 minute at a constant pressure without filtration (mL/min)
$\mu_P$: Viscosity of the platelet solution (Pa·s)
$\mu_w$: Viscosity of the physiological saline (Pa·s).

The inlet wall shear rate γ means the wall shear rate calculated from the flow rate of the platelet solution before filtration at the inlet site where contact of the platelet solution with the membrane first occurs. The wall shear rate means the shear rate on the membrane surface. The shear rate indicates the velocity gradient of the linear velocity in the direction parallel to the membrane surface, and increases as the distance from the center of the flow increases, reaching the maximum on the membrane surface. Since the cake is formed on the membrane surface, it can be said that the wall shear rate is also important for suppression of the cake. We discovered that the inlet wall shear rate is especially important. This may be because, when platelets or proteins are activated in the vicinity of the inlet of the membrane, their attachment to the membrane surface easily occurs in the downstream, leading to formation of a cake. On the other hand, activation of platelets occurs also if the wall shear rate is too high. Thus, the inlet wall shear rate is preferably not less than 25 second$^{-1}$, more preferably not less than 100 second$^{-1}$, still more preferably not less than 600 second$^{-1}$. The inlet wall shear rate is preferably not more than 1500 second$^{-1}$, more preferably not more than 1000 second$^{-1}$.

The higher the viscosity of the platelet solution, $\mu_P$, the stronger the force which suppresses cake formation. On the other hand, if the viscosity is high, the concentrations of platelets and proteins are high and, therefore, activation of platelets is likely to occur, leading to formation of a cake. Taking these facts into account, the viscosity of the platelet solution is preferably not less than $1.0 \times 10^{-3}$ Pa·s, more preferably not less than $1.2 \times 10^{-3}$ Pa·s. The viscosity of the platelet solution is preferably not more than $2.5 \times 10^{-3}$ Pa·s, more preferably not more than $1.8 \times 10^{-3}$ Pa·s. The viscosity of an arbitrary solution can be measured by an ordinary method using a commercially available measuring apparatus.

The filtration flow rate per unit area, B, is the value calculated by dividing the set filtration flow rate by the area of the membrane in contact with the platelet solution. The smaller the filtration flow rate per unit area, the weaker the force which causes formation of a cake. On the other hand, the efficiency of removal of blood plasma from the platelet solution (and the efficiency of protein removal, as a result) decreases. Taking these facts into account, the filtration flow rate per unit area is preferably 4,800 mL/hr/m$^2$ to 48,000 mL/hr/m$^2$, more preferably 14,400 mL/hr/m$^2$ to 32,000 mL/hr/m$^2$.

When a cake is formed, the actual filtration flow rate may be lower than the set flow rate, or the amount of proteins removed may be low. In such cases, the transmembrane pressure difference (hereinafter referred to as TMP) is large. In particular, once a cake is formed, cake formation accelerates. Thus, it is preferred to carry out filtration at a transmembrane pressure difference of preferably not more than $5.0 \times 10^3$ Pa, more preferably not more than $3.0 \times 10^3$ Pa. TMP can be calculated according to Formula (6):

$$TMP(Pa) = ((Pi + Po)/2) - PF \quad (6)$$

Pi: Pressure of the platelet solution supplied (Pa)
Po: Pressure of the platelet solution discharged without filtration (Pa)
PF: Pressure of the solution filtered and discharged (Pa).

In a membrane suitable to achieve the above conditions, the average pore size on the membrane surface which contacts with the platelet solution is not less than 0.1 μm and less than 2 μm, preferably not less than 0.3 μm and not more than 1.0 μm. Since proteins need to be removed as much as possible, the pore size on the membrane surface is preferably as large as possible. On the other hand, the pore size on the membrane surface needs to be smaller than the size of a platelet, which has a size of 2 to 4 μm. Taking into account the sizes of proteins and platelets, the pore size described above is most suitable for removal of proteins from the platelet solution by carrying out filtration of the platelet solution without allowing formation of a cake.

As the opening ratio on the membrane surface increases, approach routes into the membrane increase even at the same pore size so that formation of the cake layer becomes less likely to occur. The opening ratio on the membrane surface is preferably not less than 10%, more preferably not less than 12%, still more preferably not less than 15%. When the opening ratio on the surface of the separation membrane is less than 10%, a remarkable decrease in the permeation performance may occur to cause an increase in the transmembrane pressure difference, leading to activation of platelets and a low platelet recovery rate. When the opening ratio is too high, the strength of the membrane is insufficient and, therefore, the opening ratio is preferably not more than 30%, more preferably not more than 20%. The pore size and the opening ratio on the membrane surface can be determined by carrying out image processing of an image obtained with an electron microscope at a magnification of 1000×, using known software such as Matrox Inspector 2.2 (Matrox Electronic Systems Ltd.). Details of the measurement method are described later.

As permeability of the membrane increases, formation of the cake layer becomes less likely to occur so that the transmembrane pressure difference can be kept lower. That is, use of a membrane having a high permeation performance leads to suppression of platelet activation and improvement of the platelet recovery rate. Taking into account removal of as much blood plasma as possible within a high shear rate range, permeation performance of the membrane is preferably not less than 35 mL/hr/m$^2$/Pa, more preferably not less than 70 mL/hr/m$^2$/Pa. Permeation performance of the membrane is also preferably not more than 150 mL/hr/m$^2$/Pa. Permeation performance of the membrane can be determined by measuring the amount of water that flows out through the membrane per unit time at a constant pressure. Details of the measurement method are described later.

The shape of the separation membrane is not limited. The above conditions can be most efficiently achieved by allowing the platelet solution to flow in a narrow channel. A hollow fiber is most suitable as the shape of the separation membrane, and the filtration is preferably carried out by internal-pressure-type cross-flow filtration.

Although filtration by an external-pressure method using a hollow fiber membrane does not cause a problem, the gap between hollow fiber membranes needs to be as small as possible in such a case. In addition, from the viewpoint of suppressing platelet cake formation and maintaining fluidity of the platelet solution, some means to avoid contacting between the hollow fiber membranes is required. Examples of the method of avoiding contact between the hollow fiber membranes include inclusion of spacer fibers into the fiber bundle, use of a hollow fiber whose outer cross-section has a complex shape such as a star shape, and use of a hollow fiber having a wavy shape in the fiber direction.

When a hollow fiber membrane is used in internal-pressure-type cross-flow filtration, the shear rate is likely to increase as the inner membrane diameter decreases. On the other hand, if the inner membrane diameter is too small, the risk of clogging of the membrane lumen itself is high so that attention should be paid to the inner membrane diameter. Taking this fact into account, the inner membrane diameter of the hollow fiber is preferably 100 to 500 μm, more preferably 200 to 350 μm. The inner diameter of the hollow fiber membrane can be calculated by measuring the outer diameter and membrane thickness of the hollow fiber membrane. Details of the measurement process are described later.

When a hollow fiber membrane is used in internal-pressure-type cross-flow filtration, the filtration flow rate per unit membrane area, B, varies depending on the effective length of the membrane. As the effective length of the membrane increases, the filtration flow rate per unit membrane area decreases so that the cake formation can be more efficiently suppressed. However, from the viewpoint of platelet activation, the longer the effective length of the membrane, the longer the length of time during which the solution stays in the hollow fiber lumen, that is, the length of time during which platelets are in contact with the membrane surface. Thus, platelets are more likely to be activated. In view of this, the effective length of the hollow fiber membrane is preferably 5 to 50 cm, more preferably 20 to 35 cm.

The effective length means the length of the portion which effectively functions as a separation membrane. In a module packed with a membrane, the membrane is partially embedded in a potting agent or the like. Filtrate cannot pass through such an embedded portion, and thus such a portion is not included in the effective length. In a hollow fiber membrane, the length of the fiber of the effectively functioning portion of the hollow fiber membrane corresponds to the effective length. In a flat membrane which has the longitudinal length and the lateral length, the length in the same direction as the direction of the flow of the platelet solution corresponds to the effective length.

The material of the separation membrane is not limited as long as the material satisfies the conditions described above. The material is preferably a material which does not allow the membrane to activate platelets upon contacting of the membrane with the platelets, that is, a material having the so-called blood compatibility. Examples of the material include regenerated celluloses such as cellulose acetate, which is used for hemodialysis membranes and plasma separation membranes; and synthetic polymers such as ethylene-vinyl alcohol copolymers and polysulfones.

In particular, among the membrane materials described above, separation membranes using as a major material the so-called polysulfone polymer such as polysulfone or polyether sulfone are known to have excellent permeation performance and fractionation performance. Also, polysulfone polymers are most preferably used. The "polysulfone polymer" herein means a polymer containing in its main chain an aromatic ring, sulfonyl group, and ether group.

Examples of the polysulfone polymer include polysulfones represented by General Formula (I), polysulfones represented by General Formula (II), and polyethersulfones and polyallylether sulfones. Among these, polysulfones represented by General Formula (I) and polysulfones represented by General Formula (II) are preferred, and these polysulfones wherein n is 50 to 80 is more preferred. The term "polysulfone polymer" also include block copolymers between a polysulfone(s) represented by General Formula (I) or (II) and (an)other monomer(s); and modified products of polysulfones represented by General Formula (I) or (II). The ratio of the structure derived from "(an)other monomer(s)" in the block copolymer between a polysulfone(s) represented by General Formula (I) or (II) and (an)other monomer(s) is preferably not more than 10% by mass with respect to the whole block copolymer.

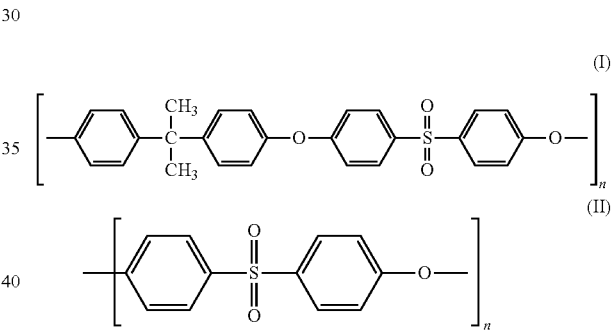

It is also known that a membrane having excellent blood compatibility can be prepared by kneading of a hydrophilic polymer with the membrane material polymer, or by modification of the membrane surface with a hydrophilic polymer. Also, the separation membrane preferably contains a hydrophilic polymer(s). The "hydrophilic polymer" means a water-soluble polymer compound or a macromolecule that interacts with water molecules by electrostatic interaction or hydrogen bonds even if the macromolecule is water-insoluble. Examples of the hydrophilic polymer herein include polyalkylene oxide, polyvinyl alcohol, polyethylene glycol, and polyvinyl pyrrolidone (hereinafter referred to as "PVP"). PVP is especially preferred.

Examples of the PVP which may be added as a hydrophilic polymer substance include PVPs having weight average molecular weights of about 6,000 (corresponding to K-15) to 1,200,000 (corresponding to K-90). When PVP is used, the weight average molecular weight of the PVP is preferably not less than 10,000, more preferably not less than 40,000, to achieve enhanced hydrophilicity.

When a separation membrane using as major materials a polysulfone polymer(s) and a hydrophilic polymer(s) is used, abundance of the hydrophilic polymer(s) in the outermost layer portion on the side which contacts with the platelet solution is preferably 30 to 60% by mass, more preferably 50 to 60% by mass. In a platelet solution, if the abundance of the hydrophilic polymer(s) in the outermost layer portion of the separation membrane is not less than 30% by mass, high hydrophilicity on the membrane surface and favorable blood compatibility can be achieved. Thus, platelet aggregation on the surface of the separation membrane can be favorably prevented, and a decrease in the separation performance of the separation membrane can be prevented. When the abundance of the hydrophilic polymer(s) in the outermost layer portion of the separation membrane is not less than 50% by mass, even higher hydrophilicity can be achieved, and the aggregation hardly occurs, which is more preferred. On the other hand, when the abundance of the hydrophilic polymer(s) in the outermost layer portion of the separation membrane is not more than 60% by mass, the amount of the hydrophilic polymer(s) eluted into the platelet solution can be kept low so that the influence of the eluted hydrophilic polymer(s) can be reduced.

The outermost layer portion of the separation membrane means an area determined by measurement by X-ray photoelectron spectroscopy (XPS) at a measurement angle of 90°. More specifically, in this method, the abundance of the hydrophilic polymer(s) between the surface and a depth of up to about 10 nm (100 Å) can be measured. For example, when the platelet solution is allowed to flow through the inside of a hollow fiber membrane, the "abundance of the hydrophilic polymer(s) in the outermost layer portion of the separation membrane" can be calculated by investigating the abundance ratios of elements such as carbon atoms and nitrogen atoms on the inner surface of the hollow fiber membrane. Details of the process are described later.

The phrase "a hydrophilic polymer is present on the membrane surface" means a state where a hydrophilic polymer stays, in a certain form, on the membrane surface of the polysulfone separation membrane which contacts with, or which does not contact with, the platelet solution. Any mode may be employed as long as the mode satisfies the above-described abundance of the hydrophilic polymer(s) in the outermost layer portion of the membrane on the side which contacts with the platelet solution, and examples of the mode include various modes such as a mode in which the hydrophilic polymer(s) is(are) covalently bound to the membrane surface of the polysulfone separation membrane which contacts with or does not contact with the platelet solution, a mode in which a layer with high hydrophilic polymer content is formed by using, in the membrane formation process, a hydrophilic polymer solution for the side which contacts with the platelet solution, and a mode in which a hydrophilic polymer coating is formed by post-coating.

Specific examples of the method of allowing the hydrophilic polymer(s) to be present on the membrane surface include the following methods. When wet membrane formation from a membrane-forming liquid is carried out, high-molecular-weight polymers tend to accumulate on the surface so that the entropy loss is prevented, and hydrophilic polymers tend to accumulate on the surface so that enthalpy loss is prevented. Accordingly, for example, in a polysulfone membrane, preparation of a binary polymer liquid composed of polysulfone(s) and a hydrophilic polymer(s) allows concentration of the hydrophilic polymer liquid on the surface so that the hydrophilic polymer(s) can be localized on the surface by carrying out polymerization. When the separation membrane is a hollow fiber membrane, an injection liquid is allowed to flow through the inside during discharging from a bicylindrical nozzle. The hydrophilic polymer(s) may be added to this injection liquid. This allows phase separation of the hollow fiber membrane, and dispersion of the hydrophilic polymer(s) contained in the injection liquid into the membrane-forming-liquid side before determination of the membrane structure so that the hydrophilic polymer(s) can be localized on the inner surface. Or, after formation of the hollow fiber membrane, the functional-layer surface of the separation membrane may be coated with the hydrophilic polymer(s). This method can be used simply and favorably. After the coating, cross-linking of the hydrophilic polymer(s) to the separation membrane may be carried out by radiation, heat treatment or the like. By this, elution of the hydrophilic polymer(s) can be more favorably suppressed. The hydrophilic polymer(s) may also be immobilized on the hollow fiber membrane by chemical reaction.

In the filtering step, a platelet solution is allowed to flow in an appropriate separation module for a platelet solution (more specifically, for example, a column equipped with a separation membrane such as the hollow fiber membrane described above) under the conditions indicated by Formula (1), thereby removing a part of the medium (mainly blood plasma) from the platelet solution by filtration. As a result, a concentrated platelet solution in which platelets are concentrated in the solution can be obtained. As long as the conditions of Formula (1) are satisfied, the degree of concentration is not limited. Normally, the medium is removed such that an about several-fold to several ten-fold decrease in the volume of the platelet solution is achieved.

This concentration step is also useful as a method of producing a concentrated platelet solution or a method of concentrating a platelet solution, which method allows highly efficient removal of proteins while suppressing activation of platelets.

After the concentration step, a mixing step in which an artificial preservation solution is added is carried out to obtain a platelet solution replaced with an artificial preservation solution. The amount of the artificial preservation solution to be added is not limited, and may be selected such that an appropriate platelet concentration can be achieved depending on the purpose of use of the obtained platelet solution replaced with an artificial preservation solution. Normally, the artificial preservation solution is added such that the volume of the resulting solution is from about one-fourth of the volume of the original platelet solution to a volume almost equivalent to the volume of the original platelet solution.

Prior to the mixing step, a recovering step of recovering platelets remaining on the separation membrane may be carried out. When the recovering step is carried out, the artificial preservation solution is brought into contact with the separation membrane that was used in the filtering step, and platelets remaining on the separation membrane are collected together with the artificial preservation solution. The resulting platelet-containing artificial preservation solution, wherein the platelets are contained in the artificial preservation solution, is used as the artificial preservation solution in the mixing step. By introduction of the recovering step, platelets remaining on the separation membrane on the side where the platelet solution enters, and platelets remaining in the pores of the separation membrane, can be recovered, and the platelet recovery rate can therefore be increased.

In the recovering step, the artificial preservation solution is brought into contact with the separation membrane that was used in the filtering step. The method of bringing the artificial preservation solution into contact with the membrane is not limited. Examples of the method include a method in which the artificial preservation solution is brought into contact, without filtration through the separation membrane, with the surface of the separation membrane which contacts with the fed platelet solution, and platelets remaining on the separation membrane are allowed to be contained in the artificial preservation solution, followed by recovering the solution containing the platelets; a method in which the artificial preservation solution is filtered through the separation membrane, and platelets remaining in the pores are allowed to be contained in the artificial preservation solution, followed by recovering the solution containing the platelets; and a method in which cross-flow filtration of the artificial preservation solution through the separation membrane is carried out to recover platelets into the artificial preservation solution while removing blood plasma remaining on the surface and in the pores of the separation membrane to the outside of the membrane, followed by recovering the solution containing the platelets. Any of these methods may be used, and two or more of these methods may be carried out in combination, if appropriate. In particular, the method in which cross-flow filtration of the artificial preservation solution is carried out followed by recovering the solution is preferred. By this method, the platelet recovery rate can be especially increased.

In the recovering step, the recovery may be carried out while changing the flow rate of the artificial preservation solution fed to the separation membrane.

In the recovering step, the flow rate is preferably controlled such that the shear rate is within the same range as in Formula (1). The filtration flow rate per unit membrane area is preferably set to a flow rate which is not more than the flow rate employed in the filtering step. By employing a filtration flow rate per unit membrane area which is equivalent to or lower than the filtration flow rate in the filtering step, platelets remaining on the surface and in the pores of the separation membrane can be recovered in the recovering step without promoting activation of the platelets. In addition, the same operation may be carried out again using, as a feed solution, the obtained platelet solution replaced with an artificial preservation solution. Repeating of the operation is preferred in view of increasing the protein removal rate. However, since repeating of the operation leads to a decrease in the platelet recovery rate, the number of times of repeating the operation is preferably up to 5, more preferably up to 3.

The number of platelets contained in each of the platelet solution to be subjected to the method, the concentrated platelet solution obtained in the filtering step, and the platelet-containing artificial preservation solution obtained in the recovering step, can be measured using a known full automatic hemocytometer (e.g., Celltac a (MEC-6318), manufactured by Nihon Kohden Corporation) or the like. The platelet recovery rate can be calculated according to Formula (7):

$$\text{Platelet recovery rate (\%)} = (I+J)/K \times 100 \quad (7)$$

I: Number of platelets contained in the concentrated platelet solution
J: Number of platelets contained in the platelet-containing artificial preservation solution
K: Number of platelets contained in the platelet solution.

Examples of indicators of activation of platelets include the ratio of CD62P-positive platelets. When platelets are activated by an external stimulus or the like, CD62P migrates to the surface of the cell membrane of platelets to be expressed. Thus, the degree of platelet activation can be evaluated based on the ratio of platelets expressing CD62P. The ratio of CD62P-positive platelets can be measured using a flow cytometer as described later in detail.

Examples of methods useful to evaluate the quality of the platelet solution to be subjected to the method and the quality of the platelet solution replaced with an artificial preservation solution obtained by the method include the swirling test. The swirling means a phenomenon in which a spiral pattern can be observed when a platelet-containing solution placed in a container is gently stirred while the container is held against light. Non-activated platelets are disk-shaped, and stirring of the disk-shaped platelets causes uniform refraction of light to cause light scattering, resulting in occurrence of swirling. If the platelet shape is changed due to activation of the platelets, the light scattering does not occur, and thus the swirling decreases and disappears.

In the measurement of the protein concentration, a conventional method of measuring total protein may be used as it is. Examples of the method of measuring total protein include various methods such as ultraviolet absorption spectrometry, and coloring methods are commonly used. Coloring methods can be roughly classified into methods using a chemical bond between a protein and a coloring dye such as the Bradford method, and methods using a chelate complex of a reduced copper ion generated in the presence of a protein such as the bicinchoninic acid (BCA) method. The method of measuring the protein concentration is not limited, and the BCA method is most preferred from the viewpoint of the accuracy. Details of the BCA method are described later.

The protein removal rate can be calculated according to Formula (8):

$$\text{Protein removal rate (\%)} = \{(O \times U) - (V \times W)\} \times 100 / (O \times U) \quad (8)$$

O: Protein concentration in the platelet solution (mg/mL)
U: Amount of the platelet solution (mL)
V: Protein concentration in the platelet solution replaced with an artificial preservation solution (mg/mL)
W: Amount of the platelet solution replaced with an artificial preservation solution (mL).

The methods of measuring the parameters are described below in detail.

(1) Measurement of Permeation Performance

The "permeation performance of the membrane" can be measured and calculated by the following method. Irrespective of whether the membrane is a flat membrane or hollow fiber membrane, the permeation performance of the membrane can be determined basically according to the same formula, i.e., Formula (9). For example, in a hollow fiber membrane, the hollow fiber membrane is inserted into a plastic tube, and both ends of the hollow fiber membrane are fixed by adhesion to the inner walls of both ends of the plastic tube, to prepare a module having an effective length of 10 cm. Water is then filtered under pressure through the module in the same direction as the filtration direction employed in the filtering step. For example, when filtration is carried out from the inside of the hollow fiber membrane to its outside, a water pressure of $1.3 \times 10^4$ Pa is applied from the inside, and the amount of water that flows out to the outside of the hollow fiber membrane per unit time is measured, followed by calculating the "permeation performance of the separation membrane" according to Formula (9):

$$\text{Permeation performance (mL/hr/Pa/m}^2\text{)} = QW/(T \times P \times X) \quad (9)$$

QW: Amount of water that flowed out to the outside of the hollow fiber membrane (mL)
T: Length of time during which water pressure was applied (hr)
P: Water pressure (Pa)
X: Area of the inner surface of the hollow fiber membrane ($m^2$).

Similarly, when a membrane having a shape different from a hollow fiber such as a flat membrane, is used, an inlet and outlet is provided in such as a plastic case. In preparation of the module, channels are closed such that there are no channels other than those passing through the membrane. Under the same conditions as described above, a water pressure of $1.3 \times 10^4$ Pa is applied from the inlet side in the direction from one surface of the membrane to the other side, and the amount of water that flows out from the other surface of the membrane per unit time is measured. Thereafter, according to Formula (9), "permeation performance of the separation membrane" can be calculated. In this case, X in Formula (9) is the surface area ($m^2$) of the portion of the separation membrane which contacts with water in the channel, and can usually be regarded as the cross-sectional area of the channel.

(2) Measurement of Inner Diameter of Hollow Fiber Membrane

The inner diameter of the hollow fiber membrane, Ri, can be calculated according to Formula (10):

$$Ri(\mu m) = Ro - 2 \times Y \quad (10)$$

Ro: Outer diameter of the hollow fiber membrane ($\mu m$)
Y: Thickness of the hollow fiber membrane ($\mu m$).

The "outer diameter of the hollow fiber membrane" is the average of values obtained by measurement of the outer diameter of each of a plurality (for example, 16) of randomly selected hollow fiber membranes using a laser displacement meter (e.g., LS5040T (Keyence Corporation) can be used). The "thickness of the hollow fiber membrane" is the average of values obtained by measurement of the membrane thickness of each of a plurality (for example, 16) of randomly selected hollow fiber membranes using a Microwatcher ×1000 lens (e.g., VH-Z100 (Keyence Corporation) can be used).

(3) Measurement of Pore Size and Opening Ratio on Membrane Surface

The "average pore size of the pores present on the surface" can be measured and calculated by the following method. First, a 10,000× image of the surface of the separation membrane is taken using a scanning electron microscope (e.g., S-800 (Hitachi, Ltd.) can be used). The brightness and contrast of the image are adjusted using an automatic function of the apparatus. Subsequently, the pore portions are painted black using known software (e.g., Microsoft Paint (Microsoft Ltd.) can be used). The image is then binarized, and subjected to image processing using known software (e.g., Matrox Inspector 2.2 (Matrox Electronic Systems Ltd.) can be used) in which the color of the pore portions is reversed to white and the color of other portions is reversed to black, followed by determining the number of the white pores (hereinafter referred to as "total pore number") and the total pixel number in the white pore portions (hereinafter referred to as "total pore area"), and then calculating the average pore size per image according to Formula (11). These measurement operations may be repeated for, e.g., 10 random sites in each of 5 hollow fibers, that is, repeated 50 times in total, to obtain the average for a total of 50 images to provide the "average pore size of the pores present on the inner surface." The black-and-white binarized image is compared to its original image to confirm that there is no discrepancy in the pore positions. In scanning electron micrographs, pores are often found inside pores (see FIG. 1A). In such cases, image processing is performed such that the pores on the outermost surface are given priority (see FIG. 1B) in calculation of the "average pore size of the pores present on the surface." In cases where the whole area of a pore is not included in the image and the image lacks an edge of the pore, the area observable in the image is subjected to the calculation. Pores having a diameter of less than 0.05 $\mu m$ are not subjected to the calculation since such pores may be generated due to noise.

$$\text{Average pore size } (\mu m) = 2 \times (\text{total pore area/total pore number}/\pi)^{0.5} \quad (11)$$

$\pi$: circular constant (–)

The imaging conditions for taking the 10,000× image may be, for example, as follows:

Imaging Conditions
Image size: 655×740 pixels
Image resolution: 0.0143 $\mu m$/pixel
Image area: 93.0 $\mu m^2$ (longitudinal length, 9.37 $\mu m$×lateral length, 9.93 $\mu m$).

It is preferred that deterioration of permeation performance be more suppressed during filtration of the platelet solution. One of the factors that significantly affect permeation performance is the opening ratio of the surface of the separation membrane. The opening ratio of the membrane surface may be measured by the same method as that for the "average pore size of the pores present on the surface" described above, and the opening ratio per image may be calculated according to Formula (12). These measurement operations may be repeated for, e.g., 10 random sites on each of 5 hollow fibers, that is, repeated 50 times in total, to obtain the average for a total of 50 images to provide the "surface opening ratio."

$$\text{Opening ratio (\%)} = \text{total pore area/image size} \times 100 \quad (12)$$

(4) Measurement of Abundance of Hydrophilic Polymer(s)

The membrane surface that contacts with the platelet solution is exposed, and rinsed with ultrapure water, followed by drying the membrane at room temperature at 0.5 Torr for 10 hours to provide a measurement sample. The sample is placed in an X-ray photoelectron spectroscope (e.g., ESCALAB 220i-XL, manufactured by Thermo Fisher Scientific K. K., can be used), and measurement is carried out at a measurement angle of 90° by adjusting the angle of the detector with respect to the angle of incidence of the X-ray. From the integrated intensity of each of the C1s, N1s, and S2p spectra obtained and the relative sensitivity coefficient belonging to the apparatus, the abundance ratios of carbon atoms, nitrogen atoms, and sulfur atoms in the portion from the outer surface to a depth of about 10 nm in the hollow fiber membrane are calculated.

For example, when the membrane material is polysulfone represented by Formula (1) and the "hydrophilic polymer on the surface of the membrane on the side which contacts with the platelet solution" is PVP, the measurement using XPS may be carried out at a measurement angle of 90° to investigate the abundance ratios of carbon atoms, nitrogen atoms and sulfur atoms in the portion from the surface of the membrane to a depth of about 10 nm on the side of the separation membrane which contacts with the platelet solution, followed by calculating the abundance of the hydrophilic polymer present in the outermost layer portion of the separation membrane according to Formula (13):

$$\text{Abundance of the hydrophilic polymer in the outermost layer portion of the separation membrane (\% by mass)} = N \times 111/(N \times 111 + S \times 442) \times 100 \quad (13)$$

N: Abundance ratio of nitrogen atoms
S: Abundance ratio of sulfur atoms
111: Molecular weight of repeat unit of PVP 442: Molecular weight of repeat unit of polysulfone polymer.

(5) Measurement of Ratio of CD62P-Positive Platelets

In measurement of the ratio of CD62P-positive platelets, sampling is carried out within 5 minutes after production of the platelet solution replaced with an artificial preservation solution, and the sample is fixed using 1% paraformaldehyde/PBS solution. The fixed platelets within 12 hours to 1 week after the fixation are used as a measurement sample. The measurement sample is washed with PBS, and the platelet number is adjusted, followed by providing (i) a sample supplemented with a CD61 antibody, which is an antibody against an activation-independent platelet-specific marker, and control IgG; and (ii) a sample supplemented with the CD61 antibody and a CD62P antibody. After addition of the antibodies, the samples (i) and (ii) are left to stand for 20 minutes in the dark. Subsequently, CellFix, which is a fixation reagent manufactured by Becton, Dickinson and Company, 10-fold diluted with pure water, is added to each of the samples (i) and (ii), and the resulting samples are left to stand overnight. Thereafter, PBS is added to each sample, and centrifugation of the resulting mixture is carried out at 2000×g for 10 minutes, followed by washing. For the measurement, the sample (i) is first subjected to flow cytometry. Platelets are gated by the scattering light pattern, and gating of platelets is also carried out using a fluorescent label of CD61. Thereafter, using a fluorescent label of the control IgG, a cut-off line is set such that 0.5% to 1.0% of platelets show positivity. While the gate and cut-off line are fixed, the sample (ii) is then subjected to the measurement in the same manner, and the ratio of the number of platelets which exceeded the cut-off line is defined as the ratio of CD62P-positive platelets.

(6) Measurement of Protein Concentration Using BCA Method

Measurement of the protein concentration by the BCA method can be easily carried out using BCA kits commercially available from various manufacturers. The platelet solution and the platelet solution replaced with an artificial preservation solution are sampled within 5 minutes, and the sample is used within 24 hours after the sampling. The sampled platelet solution and platelet solution replaced with an artificial preservation solution are subjected to centrifugation at 2000×g for 10 minutes, and the supernatants from which platelets have been removed are used as measurement samples. The measurement samples are stored at 4° C., and subjected to the measurement within 1 week after the sampling. In the measurement, BCA reagent and samples for a calibration curve are prepared. According to the instructions of the kit, BCA reagent is added to the calibration curve samples and the measurement samples, and the resulting mixtures are stirred using a micromixer at room temperature for 30 seconds. Thereafter, the samples are incubated at 37° C. for 30 minutes, and the sample temperature was then lowered to room temperature, followed by measurement of the absorbance of each sample at a wavelength of 562 nm. The wavelength for the measurement of the absorbance does not need to be strictly the same as long as the wavelength is within the range of the above-described wavelength ±about 20 nm. The results from the calibration curve samples are used to draw a calibration curve for the protein concentration and the absorbance. The protein concentration in each measurement sample can be determined by assigning the absorbance of the measurement sample to the formula of the calibration curve.

EXAMPLES

Our methods are described below in detail by way of Examples. However, this disclosure is not limited to these Examples. Measurements of the permeation performance, inner diameter of the hollow fiber membrane, pore size and opening ratio on the membrane surface, abundance of the hydrophilic polymer, ratio of CD62P-positive platelets, and protein concentration were carried out according to the methods described in (1) to (6) above.

Preparation of Hollow Fiber Membrane

A mixture composed of 15 parts of Udel (registered trademark) polysulfone (P3500, Solvay), 8 parts of PVP (K90, ISP), 75 parts of dimethylacetamide (hereinafter referred to as "DMAc"), and 2 parts of water was mixed and dissolved at 90° C., and then incubated at 50° C. to provide a membrane-forming liquid. To a mixed solution composed of 80 parts of DMAC and 20 parts of water, 30 parts of PVP (K30, ISP) was added, and the PVP was dissolved in the solution by mixing, to provide a core liquid.

Using an orifice-type bicylindrical nozzle having an outer diameter of 1.0 mm and inner diameter of 0.7 mm, the membrane-forming liquid and core liquid were discharged at the same time from the outer cylinder and inner cylinder, respectively, and allowed to pass through a dry section at 30° C. having a length of 80 mm, followed by immersion in a coagulation bath at 90° C. containing a mixed solution of 90 parts of water and 10 parts of DMAC to allow coagulation. The resulting product was washed in warm water in a warm water bath at 80° C., and then wound into a reel, to obtain a hollow fiber membrane in the wet state. As a result of the process at a membrane formation rate of 40 m/minute, the inner diameter of the hollow fiber membrane became 300 μm and the membrane thickness of the hollow fiber membrane became 80 μm. A 10,000× image of the inner surface of the hollow fiber was obtained using a field emission scanning electron microscope S-800 (Hitachi, Ltd.). The brightness and contrast of the image were adjusted using an automatic function of the apparatus. Subsequently, the pore portions were painted black using Microsoft Paint (Microsoft Ltd.). The image was then binarized, and subjected to image processing using Matrox Inspector 2.2 (Matrox Electronic Systems Ltd.) such that the color of the pore portions was reversed to white and the color of other portions was reversed to black, followed by determining the number of the white pores and the total pore area in the white-pore portions, and then calculating the average pore size per image according to Formula (11). These measurement operations were repeated for 10 random sites on each of 5 hollow fibers, that is, repeated 50 times in total, to obtain the average value for a total of 50 images. FIG. 1A shows a representative electron micrograph, and FIG. 1B shows a binarized image of the representative electron micrograph.

The obtained hollow fiber membrane in the wet state was cut into pieces each having a length of 0.4 m and divided into batches, and each batch was washed in warm water by immersion in a warm water bath at 90° C. for 30 minutes, followed by drying treatment at 100° C. for 10 hours and then heat cross-linking treatment in a heat dryer at 170° C. for 5 hours to obtain hollow fiber membranes.

Example 1

As separation membranes, hollow fiber membranes composed of polysulfone and PVP were used.

From the hollow fiber membranes, a hollow fiber membrane module (separation membrane module for a platelet solution) was prepared as follows. First, into a cylindrical plastic module having a diameter of 18 mm and length of 310 mm, a bundle of 528 hollow fiber membranes obtained by the above-described membrane formation operations was inserted, and the resultant was immersed in 60% by mass aqueous glycerol solution, followed by drying at 50° C. for one day and night. Subsequently, the plastic module was placed in a centrifuge, and 5 mL of a urethane resin, that is, potting material, was injected to each end of the module, followed by rotating the module at 60 G/15 minutes (first potting). Fifteen minutes thereafter, 10 mL of the potting material was further injected to each end of the plastic module, and the module was rotated again at 60 G/15 minutes (second potting), to prepare a hollow fiber membrane module.

The inner diameter of the hollow fiber membranes was 300 μm; the membrane area was 0.144 m$^2$; the permeation performance was 75 mL/hr/Pa/m$^2$; the opening ratio on the inner surface was 17.3%; the average pore size was 0.90 μm; and the abundance of the hydrophilic polymer present on the inner surface was 54.2%.

Using the thus prepared hollow fiber membrane module, filtration of a platelet solution was carried out. More specifically, first, 52.2 mL of MEYLON (registered trademark) manufactured by Otsuka Pharmaceutical Co., Ltd., 126.8 mL of ACD-A solution manufactured by Terumo Corporation, 3.2 mL of Mg sulfate supplement (1 mEq/ml) manufactured by Otsuka Pharmaceutical Co., Ltd., and 71.6 mL of distilled water manufactured by Otsuka Pharmaceutical Co., Ltd. were added to 746.2 mL of SOLACET F (registered trademark) manufactured by Terumo Corporation, and the resulting mixture was mixed to prepare M-sol as an artificial preservation solution. The platelet number in the original platelet solution was measured in advance.

Using a blood pump at 67.2 mL/min., 600 mL of a platelet solution containing 2.0×10$^{11}$ platelets (platelet concentration was 33×10$^7$ platelets/mL) was subjected to cross-flow filtration by application of an internal pressure (filtering step). The viscosity of the platelet solution was 1.6 mPa·s. At this time, the filtration rate was 60.5 mL/min.; the inlet wall shear rate was 800 second$^{-1}$; the filtration flow rate per unit area was 60.5×60 (mL/hr)/0.144 (m$^2$)=25,208 mL/hr/m$^2$; and TMP was 3.0×10$^3$ Pa.

By this treatment, the platelet solution was filtered through the inside of the hollow fibers, and 60 mL of a concentrated platelet solution was obtained (filtering step). Thereafter, M-sol was allowed to flow through the inside of the hollow fibers at 67.2 mL/min, and the artificial preservation solution, in which platelets were contained, was recovered (recovering step). Thereafter, this artificial preservation solution and the concentrated platelet solution were mixed together to prepare 200 mL of a platelet solution replaced with the artificial preservation solution (mixing step). The obtained platelet solution replaced with the artificial preservation solution could achieve removal of 87% of plasma proteins from the original platelet solution. The platelet recovery rate was 93%; the ratio of CD62P-positive platelets in the platelet solution replaced with the artificial preservation solution was 10%; and swirling could be observed.

Example 2

As separation membranes, hollow fiber membranes composed of polysulfone and PVP were used.

From the hollow fiber membranes, a hollow fiber membrane module (separation membrane module for a platelet solution) was prepared as follows. First, into a cylindrical plastic module having a diameter of 10 mm and length of 220 mm, a bundle of 50 hollow fiber membranes obtained by the above-described membrane formation operations was inserted, and the resultant was immersed in 60% by mass aqueous glycerol solution, followed by drying at 50° C. for one day and night. Subsequently, the plastic module was placed in a centrifuge, and 0.5 mL of a urethane resin, that is, potting material, was injected to each end of the module, followed by rotating the module at 60 G/15 minutes (first potting). Fifteen minutes thereafter, 1.7 mL of the potting material was further injected to each end of the plastic module, and the module was rotated again at 60 G/15 minutes (second potting), to prepare a hollow fiber membrane module.

The inner diameter of the hollow fiber membranes was 300 μm; the membrane area was 0.0094 m$^2$; the permeation performance was 75 mL/hr/Pa/m$^2$; the opening ratio on the inner surface was 17.3%; the average pore size was 0.90 μm; and the abundance of the hydrophilic polymer present on the inner surface was 54.2%.

Using the thus prepared hollow fiber membrane module, filtration of a platelet solution was carried out. More specifically, first, 52.2 mL of MEYLON manufactured by Otsuka Pharmaceutical Co., Ltd., 126.8 mL of ACD-A solution manufactured by Terumo Corporation, 3.2 mL of Mg sulfate supplement (1 mEq/ml) manufactured by Otsuka Pharmaceutical Co., Ltd., and 71.6 mL of distilled water manufactured by Otsuka Pharmaceutical Co., Ltd. were added to 746.2 mL of SOLACET F manufactured by Terumo Corporation, and the resulting mixture was mixed to prepare M-sol as an artificial preservation solution. The platelet number in the original platelet solution was measured in advance.

Using a blood pump at 3.2 mL/min, 16.2 mL of a platelet solution containing 1.78×10$^{10}$ platelets (platelet concentration was 110×10$^7$ platelets/mL) was subjected to cross-flow filtration by application of an internal pressure (filtering step). The viscosity of the platelet solution was 1.9 mPa·s. At this time, the filtration rate was 2.5 mL/min; the inlet wall shear rate was 400 second$^{-1}$; the filtration flow rate per unit area was 2.5×60 (mL/hr)/0.0094 (m$^2$)=15,957 mL/hr/m$^2$; and TMP was 4.5×10$^3$ Pa.

By this treatment, the platelet solution was filtered through the inside of the hollow fibers, and 3.24 mL of a concentrated platelet solution was obtained. Thereafter, M-sol was allowed to flow through the inside of the hollow fibers at 3.2 mL/min, and the artificial preservation solution, in which platelets are contained, was recovered (recovering step). Thereafter, this artificial preservation solution and the concentrated platelet solution were mixed together to prepare 16.2 mL of a platelet solution replaced with the artificial preservation solution (mixing step). The obtained platelet solution replaced with the artificial preservation solution could achieve removal of 73% of plasma proteins from the original platelet solution. The platelet recovery rate was 94%; the ratio of CD62P-positive platelets in the platelet solution replaced with the artificial preservation solution was 30%; and swirling could be observed.

Example 3

As separation membranes, the same hollow fiber membranes composed of polysulfone and PVP as in Example 1 were used. In the same manner as in Example 1, a hollow fiber membrane module was prepared.

Using the thus prepared hollow fiber membrane module, filtration of a platelet solution was carried out. More specifically, first, 52.2 mL of MEYLON manufactured by Otsuka Pharmaceutical Co., Ltd., 126.8 mL of ACD-A solution manufactured by Terumo Corporation, 3.2 mL of Mg sulfate supplement (1 mEq/ml) manufactured by Otsuka Pharmaceutical Co., Ltd., and 71.6 mL of distilled water manufactured by Otsuka Pharmaceutical Co., Ltd. were added to 746.2 mL of SOLACET F manufactured by Terumo Corporation, and the resulting mixture was mixed to prepare M-sol as an artificial preservation solution. The platelet number in the original platelet solution was measured in advance.

Using a blood pump at 7.5 mL/min, 200 mL of a platelet solution containing $2.0 \times 10^{11}$ platelets (platelet concentration was $100 \times 10^7$ platelets/mL) was subjected to cross-flow filtration by application of an internal pressure (filtering step). The viscosity of the platelet solution was 1.9 mPa·s. At this time, the filtration rate was 6.0 mL/min; the inlet wall shear rate was 100 second$^{-1}$; the filtration flow rate per unit area was $6.0 \times 60$ (mL/hr)/0.144 (m$^2$)=2500 mL/hr/m$^2$; and TMP was $5.0 \times 10^2$ Pa.

By this treatment, the platelet solution was filtered through the inside of the hollow fibers, and 80 mL of a concentrated platelet solution was obtained (filtering step). Thereafter, M-sol was allowed to flow through the inside of the hollow fibers at 7.5 mL/min., and the artificial preservation solution, in which platelets are contained, was recovered (recovering step). Thereafter, this artificial preservation solution and the concentrated platelet solution were mixed together to prepare 200 mL of a platelet solution replaced with the artificial preservation solution (mixing step). The obtained platelet solution replaced with the artificial preservation solution could achieve removal of 76% of plasma proteins from the original platelet solution. The platelet recovery rate was 95%; the ratio of CD62P-positive platelets in the platelet solution replaced with the artificial preservation solution was 20%; and swirling could be observed.

Comparative Example 1

As separation membranes, hollow fiber membranes composed of polysulfone and PVP were used.

From the hollow fiber membranes, a hollow fiber membrane module (separation membrane module for a platelet solution) was prepared as follows. First, into a cylindrical plastic module having a diameter of 10 mm and length of 220 mm, a bundle of 50 hollow fiber membranes obtained by the above-described membrane formation operations was inserted, and the resultant was immersed in 60% by mass aqueous glycerol solution, followed by drying at 50° C. for one day and night. Subsequently, the plastic module was placed in a centrifuge, and 0.5 mL of a urethane resin, that is, potting material, was injected to each end of the module, followed by rotating the module at 60 G/15 minutes (first potting). Fifteen minutes thereafter, 1.7 mL of the potting material was further injected to each end of the plastic module, and the module was rotated again at 60 G/15 minutes (second potting), to prepare a hollow fiber membrane module.

The inner diameter of the hollow fiber membranes was 300 μm; the membrane area was 0.0094 m$^2$; the permeation performance was 75 mL/hr/Pa/m$^2$; the opening ratio on the inner surface was 17.3%; the average pore size was 0.90 μm; and the abundance of the hydrophilic polymer present on the inner surface was 54.2%.

Using the thus prepared hollow fiber membrane module, filtration of a platelet solution was carried out. More specifically, first, 52.2 mL of MEYLON manufactured by Otsuka Pharmaceutical Co., Ltd., 126.8 mL of ACD-A solution manufactured by Terumo Corporation, 3.2 mL of Mg sulfate supplement (1 mEq/mL) manufactured by Otsuka Pharmaceutical Co., Ltd., and 71.6 mL of distilled water manufactured by Otsuka Pharmaceutical Co., Ltd. were added to 746.2 mL of SOLACET F manufactured by Terumo Corporation, and the resulting mixture was mixed to prepare M-sol as an artificial preservation solution. The platelet number in the original platelet solution was measured in advance.

Using a blood pump at 15.9 mL/min, 16.2 mL of a platelet solution containing $1.78 \times 10^{10}$ platelets (platelet concentration was $110 \times 10^7$ platelets/mL) was subjected to cross-flow filtration by application of an internal pressure (filtering step). The viscosity of the platelet solution was 1.9 mPa·s. At this time, the filtration rate was 12.7 mL/min; the inlet wall shear rate was 2000 second$^{-1}$; the filtration flow rate per unit area was $12.7 \times 60$ (mL/hr)/0.0094 (m$^2$)=81,063 mL/hr/m$^2$; and TMP was $7.0 \times 10^3$ Pa.

By this treatment, the platelet solution was filtered through the inside of the hollow fibers, and 4.2 mL of a concentrated platelet solution was obtained. Thereafter, M-sol was allowed to flow through the inside of the hollow fibers at 15.9 mL/min, and the artificial preservation solution, in which platelets are contained, was recovered (recovering step). Thereafter, this artificial preservation solution and the concentrated platelet solution were mixed together to prepare 16.2 mL of a platelet solution replaced with the artificial preservation solution (mixing step). The obtained platelet preparation could achieve removal of 61% of plasma proteins from the original platelet solution. The platelet recovery rate was 86%; the ratio of CD62P-positive platelets in the platelet solution replaced with the artificial preservation solution was 65%; and swirling could not be observed. Although the value of $(A \times B)/(\gamma \times \mu_P)$ did not exceed $2.5 \times 10^{13}$, the inlet wall shear rate exceeded the range in our methods. It is though that this lead to high platelet activity and attachment of a large amount of platelets to the membrane as a result, causing clogging of the membrane, which then resulted in the low protein removal rate.

Comparative Example 2

As separation membranes, hollow fiber membranes composed of polysulfone and PVP were used.

From the hollow fiber membranes, a hollow fiber membrane module (separation membrane module for a platelet solution) was prepared as follows. First, into a cylindrical plastic module having a diameter of 10 mm and length of 120 mm, a bundle of 50 hollow fiber membranes obtained by the above-described membrane formation operations was inserted, and the resultant was immersed in 60% by mass aqueous glycerol solution, followed by drying at 50° C. for one day and night. Subsequently, the plastic module was placed in a centrifuge, and 0.5 mL of a urethane resin, that is, potting material, was injected to each end of the module, followed by rotating the module at 60 G/15 minutes (first potting). Fifteen minutes thereafter, 1.7 mL of the potting material was further injected to each end of the plastic module, and the module was rotated again at 60 G/15 minutes (second potting), to prepare a hollow fiber membrane module.

The inner diameter of the hollow fiber membranes was 300 μm; the membrane area was 0.0047 m$^2$; the permeation performance was 75 mL/hr/Pa/m$^2$; the opening ratio on the inner surface was 17.3%; the average pore size was 0.90 μm; and the abundance of the hydrophilic polymer present on the inner surface was 54.2%.

Using the thus prepared hollow fiber membrane module, filtration of a platelet solution was carried out. More specifically, first, 52.2 mL of MEYLON manufactured by Otsuka Pharmaceutical Co., Ltd., 126.8 mL of ACD-A solution manufactured by Terumo Corporation, 3.2 mL of Mg sulfate supplement (1 mEq/ml) manufactured by Otsuka Pharmaceutical Co., Ltd., and 71.6 mL of distilled water manufactured by Otsuka Pharmaceutical Co., Ltd. were added to 746.2 mL of SOLACET F manufactured by Terumo Corporation, and the resulting mixture was mixed to prepare M-sol as an artificial preservation solution. The platelet number in the original platelet solution was measured in advance.

Using a blood pump at 5.6 mL/min, 8.1 mL of a platelet solution containing $8.9 \times 10^9$ platelets (platelet concentration was $110 \times 10^7$ platelets/mL) was subjected to cross-flow filtration by application of an internal pressure (filtering step). The viscosity of the platelet solution was 1.9 mPa·s. At this time, the filtration rate was 3.9 mL/min; the inlet wall shear rate was 700 second$^{-1}$; the filtration flow rate per unit area was $3.9 \times 60$ (mL/hr)/0.0047 (m$^2$)=49,787 mL/hr/m$^2$; and TMP was $1.0 \times 10^4$ Pa.

By this treatment, the platelet solution was filtered through the inside of the hollow fibers, and 4.1 mL of a concentrated platelet solution was obtained. Thereafter, M-sol was allowed to flow through the inside of the hollow fibers at 5.6 mL/min, and the artificial preservation solution, in which platelets are contained, was recovered (recovering step). Thereafter, this artificial preservation solution and the concentrated platelet solution were mixed together to prepare 8.1 mL of a platelet solution replaced with the artificial preservation solution (mixing step). The obtained platelet preparation could achieve removal of 40% of plasma proteins from the original platelet solution. The platelet recovery rate was 60%; the ratio of CD62P-positive platelets in the platelet solution replaced with the artificial preservation solution was 45%; and swirling could be observed. In this case, although the inlet wall shear rate was low, the value of $(A \times B)/(\gamma \times \mu_P)$ exceeded $2.5 \times 10^{13}$. It can thus be assumed that formation of a cake layer occurred to cause the decreases in the protein removal rate and platelet recovery rate. It can also be assumed that formation of the cake layer caused activation of platelets to a certain extent.

A summary of the numerical data obtained in the Examples and Comparative Examples is shown in Table 1.

TABLE 1

| | Example 1 | Example 2 | Example 3 | Comparative Example 1 | Comparative Example 2 |
|---|---|---|---|---|---|
| Average pore size (μm) | 0.90 | 0.90 | 0.90 | 0.90 | 0.90 |
| Inlet wall shear rate (second$^{-1}$) | 800 | 400 | 100 | 2000 | 700 |
| A × B/γ × μ$_p$ | $3.9 \times 10^{12}$ | $2.3 \times 10^{13}$ | $1.6 \times 10^{13}$ | $2.3 \times 10^{13}$ | $4.1 \times 10^{13}$ |
| Transmembrane pressure difference (Pa) | $3.0 \times 10^3$ | $4.5 \times 10^3$ | $5.0 \times 10^2$ | $7.0 \times 10^3$ | 10 |
| Permeation performance (mL/hr/m$^2$/Pa) | 75 | 75 | 75 | 75 | 75 |
| Inner diameter of hollow fiber membrane (μm) | 300 | 300 | 300 | 300 | 300 |
| Effective length of hollow fiber membrane (mm) | 290 | 200 | 290 | 200 | 100 |
| Abundance of hydrophilic polymer in outermost layer portion (mass %) | 54.2 | 54.2 | 54.2 | 54.2 | 54.2 |
| Plasma protein removal rate (%) | 87 | 73 | 76 | 61 | 40 |
| Platelet recovery rate (%) | 93 | 94 | 95 | 86 | 60 |
| Ratio of CD62P-positive platelets (%) | 10 | 30 | 20 | 65 | 45 |

The invention claimed is:

1. A method of producing a platelet solution wherein a large part of medium in said platelet solution is replaced with an artificial preservation solution; wherein activation of platelets is prevented and a large amount of proteins in said platelet solution are removed said method comprising:
    (a) a filtering step of carrying out an internal-pressure cross-flow filtration of said platelet solution under conditions of Formula 1 at an inlet wall shear rate of 25 to 1500 s$^{-1}$ using a separation membrane whose surface which contacts with the platelet solution has an average pore size of not less than 0.1 μm and less than 2.0 μm, thereby obtaining a concentrated platelet solution; and
    (b) a mixing step of mixing the concentrated platelet solution obtained in step (a) with an artificial preservation solution that is an infusion solution that does not induce generation of an aggregate or destruction of platelets upon contact with platelets to obtain said platelet solution:

Formula $1=1.0 \times 10^{11} < (A \times B)/(\gamma \times \mu_P) \leq 2.5 \times 10^{13}$ (platelets/(hr·m$^2$·Pa))

A: Concentration of platelets contained in the platelet solution (platelets/mL; with a proviso that the range is $8.0 \times 10^7$ to $200 \times 10^7$ platelets/mL)
    B: Filtration flow rate per unit area (mL/hr/m$^2$)
    γ: Inlet wall shear rate (s$^{-1}$)
    $\mu_P$: Viscosity of the platelet solution (Pa·s).

2. The method according to claim 1, wherein a protein removal rate is not less than 60%, and a ratio of CD62P-positive platelets in said platelet solution replaced with an artificial preservation solution is not more than 60%.

3. The method according to claim 1, wherein a transmembrane pressure difference in step (a) is not more than $5.0 \times 10^3$ Pa.

4. The method according to claim 1, wherein a permeation performance of said separation membrane is 35 to 150 mL/hr/m$^2$/Pa.

5. The method according to claim 1, wherein said separation membrane contains 30 to 60% by mass hydrophilic polymers in an outermost layer which contacts the platelet solution, as measured by X-ray photoelectron spectroscopy at a measurement angle of 90°.

6. The method according to claim 1, wherein said separation membrane is a hollow fiber membrane.

7. The method according to claim 6, wherein said hollow fiber membrane has an inner diameter of 100 to 500 μm.

8. The method according to claim 6, wherein said hollow fiber membrane has an effective length of 5 to 50 cm.

9. A method of producing a platelet solution wherein a large part of medium in said platelet solution is replaced with an artificial preservation solution; wherein activation of platelets is prevented and a large amount of proteins in said platelet solution are removed; said method comprising:
    (a) a filtering step of carrying out an internal-pressure cross-flow filtration of said platelet solution under conditions of Formula 1 at an inlet wall shear rate of 25 to 1500 s$^{-1}$ using a separation membrane whose surface which contacts with the platelet solution has an average pore size of not less than 0.1 µm and less than 2.0 µm, thereby obtaining a concentrated platelet solution; and (b) a platelet recovery step of recovering platelets remaining on said separation membrane of step (a), wherein the artificial preservation solution is brought into contact with the separation membrane and platelets remaining on the separation membrane are collected together with the artificial preservation solution, thereby obtaining a platelet-containing artificial preservation solution; and (c) a mixing step of mixing the concentrated platelet solution obtained in step (a) with the platelet-containing artificial preservation solution obtained in step (b) to obtain said platelet solution:

$$\text{Formula 1} = 1.0 \times 10^{11} < (A \times B)/(\gamma \times \mu_P) \le 2.5 \times 10^{13} \text{ (platelets/(hr·m}^2\text{·Pa))}$$

A: Concentration of platelets contained in the platelet solution (platelets/mL; with a proviso that the range is $8.0 \times 10^7$ to $200 \times 10^7$ platelets/mL)

B: Filtration flow rate per unit area (mL/hr/m$^2$)

$\gamma$: Inlet wall shear rate (s$^{-1}$)

$\mu_P$: Viscosity of the platelet solution (Pa·s).

\* \* \* \* \*